United States Patent [19]
McBrayer et al.

[11] Patent Number: 5,395,369
[45] Date of Patent: Mar. 7, 1995

[54] ENDOSCOPIC BIPOLAR ELECTROCAUTERY INSTRUMENTS

[75] Inventors: Michael S. McBrayer, Miami; Jurgen A. Kortenbach, Miami Springs; Charles R. Slater, Fort Lauderdale, all of Fla.

[73] Assignee: Symbiosis Corporation, Miami, Fla.

[21] Appl. No.: 91,177

[22] Filed: Jul. 13, 1993

Related U.S. Application Data

[63] Continuation-in-part of Ser. No. 74,790, Jun. 10, 1993.

[51] Int. Cl.⁶ ................ A61B 17/28; A61B 17/36
[52] U.S. Cl. ................ 606/51; 606/205; 128/751
[58] Field of Search .......... 606/51, 52, 50, 48, 606/207, 205, 170; 128/751

[56] References Cited

U.S. PATENT DOCUMENTS

| | | | |
|---|---|---|---|
| 2,031,682 | 2/1936 | Wappler et al. | 174/89 |
| 3,446,211 | 5/1969 | Markham | 606/207 |
| 3,920,021 | 11/1975 | Hiltebrandt | 128/303.17 |
| 4,347,842 | 9/1982 | Beale | 128/276 |
| 4,644,651 | 2/1987 | Jacobsen | 30/251 |
| 4,819,633 | 4/1989 | Bauer et al. | 606/52 |
| 4,862,890 | 9/1989 | Stasz et al. | 128/303.14 |
| 4,953,559 | 9/1990 | Salerno | 128/751 |
| 5,015,227 | 5/1991 | Broadwin et al. | 604/22 |
| 5,026,370 | 6/1991 | Lottick | 606/42 |
| 5,035,248 | 7/1991 | Zinnecker | 128/751 |
| 5,085,659 | 2/1992 | Rydell | 606/47 |
| 5,160,343 | 11/1992 | Brancel et al. | 606/205 |
| 5,171,256 | 12/1992 | Smith et al. | 606/205 |
| 5,171,311 | 12/1992 | Rydell et al. | 606/48 |
| 5,176,677 | 1/1993 | Wuchinich | 606/46 |
| 5,197,963 | 3/1993 | Parins | 606/46 |
| 5,197,964 | 3/1993 | Parins | 606/48 |
| 5,258,006 | 11/1993 | Rydell et al. | 606/205 |

FOREIGN PATENT DOCUMENTS

| | | | |
|---|---|---|---|
| 5172441 | 12/1991 | European Pat. Off. | A61B 17/39 |
| 5182301 | 12/1992 | European Pat. Off. | A61B 17/39 |

*Primary Examiner*—Michael H. Thaler
*Attorney, Agent, or Firm*—David P. Gordon

[57] ABSTRACT

An endoscopic bipolar electrocautery instrument includes a proximal actuator coupled by a tube and push rod to a pair of distal graspers. The tube is covered with an insulating shrink wrap from its distal end up to an uncovered proximal portion. A stationary jaw with an integral clevis is mounted inside the distal end of the tube and electrically contacts the inner surface thereof. The clevis holds a pair of ceramic insulators between which a movable jaw is mounted on an insulated bushing with an axle pin. The movable jaw is electrically and mechanically coupled to the push rod which is covered with an insulating shrink wrap from a point just proximal of its connection with the movable jaw to a point near its proximal end. The uninsulated proximal end of the tube is mounted in a conductive bushing which rotates within a nonconductive handle. The proximal end of the push rod extends beyond the conductive bushing and a rubber insulator is fitted between the bushing and the push rod. A nonconductive actuating lever is hingedly attached to the handle and the push rod is rotatingly coupled thereto. A pair of Y-shaped electrical wiper contacts are insert molded in a nonconductive member mounted in the handle and respectively contact the bushing and uninsulated portion of the push rod on either side of the rubber insulator. A bipolar cable insert molded in the nonconductive member is coupled to these contacts and to a source of current.

26 Claims, 8 Drawing Sheets

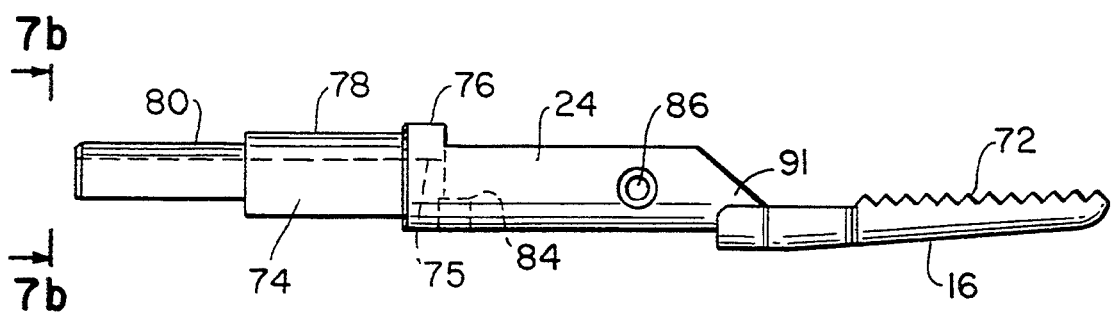
FIG. 7
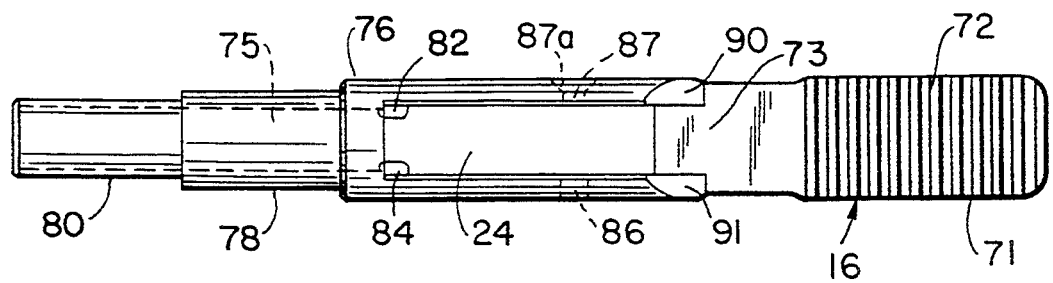
FIG. 7a
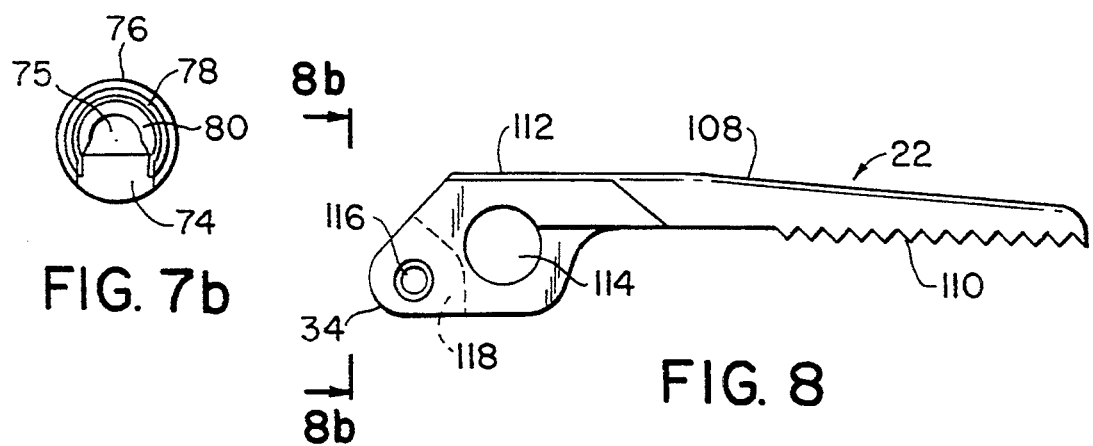
FIG. 7b
FIG. 8
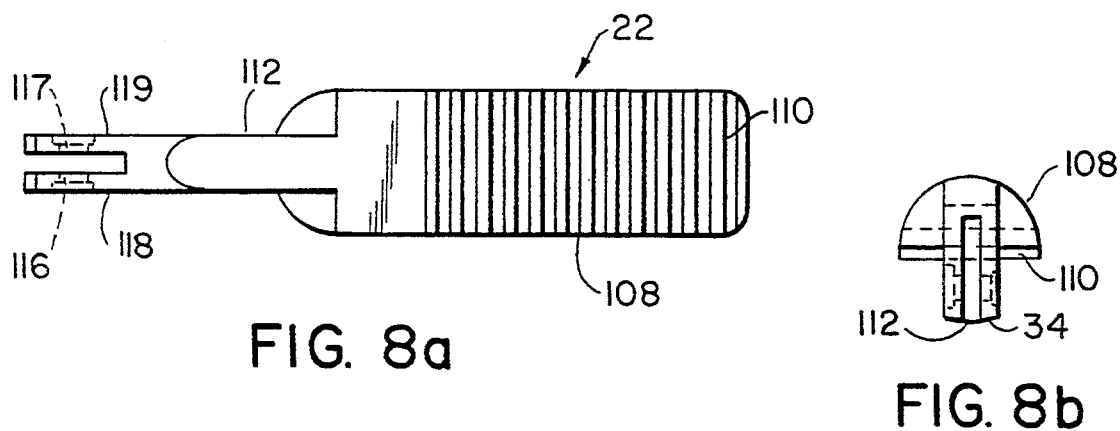
FIG. 8a
FIG. 8b

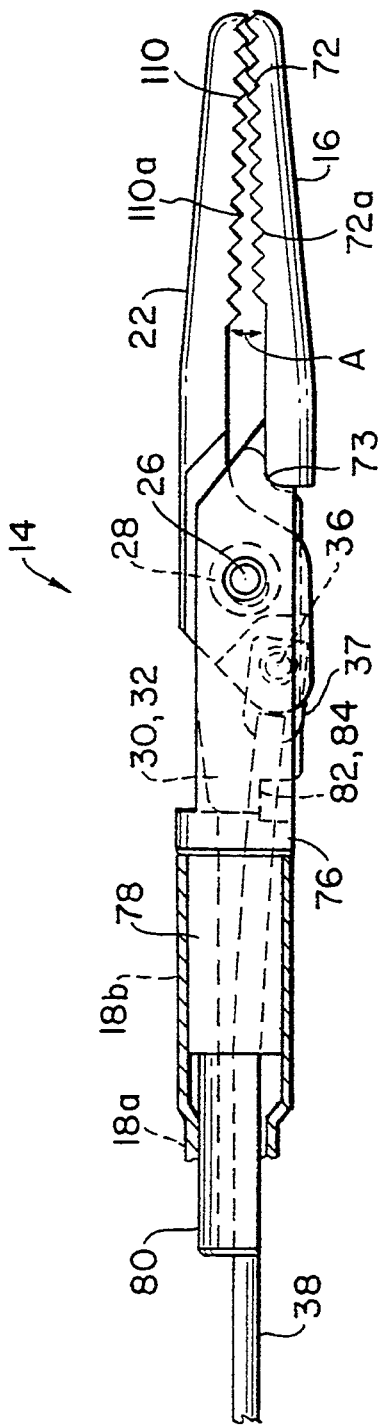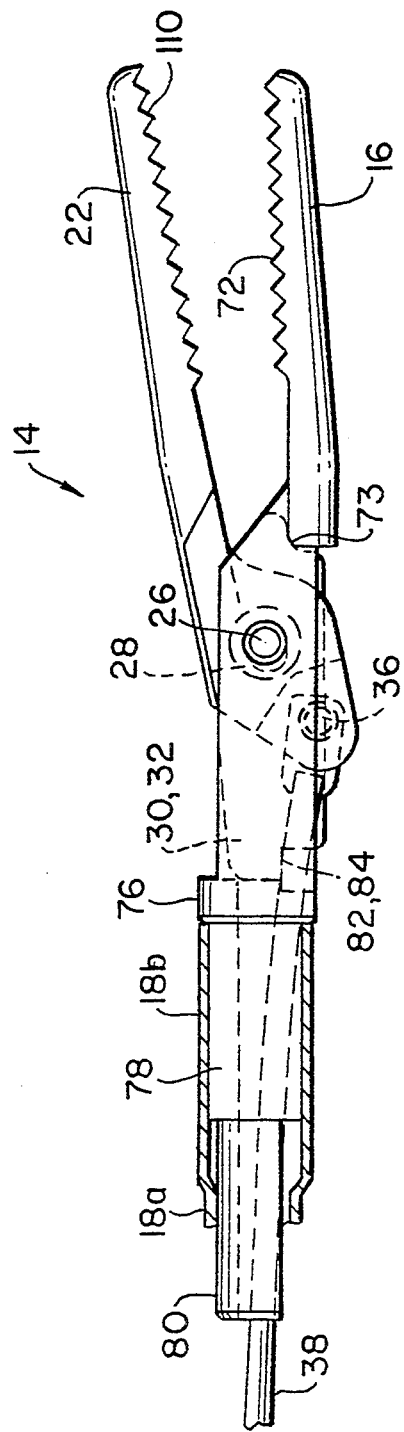

ENDOSCOPIC BIPOLAR ELECTROCAUTERY INSTRUMENTS

This application is a continuation-in-part of co-owned, Ser. No. 08/074,790, (Endoscopic Instruments Having Internal Gas Seal) filed Jun. 10, 1993, which is hereby incorporated by reference herein. This application also relates to co-owned, copending Ser. No. 07/959,280 (Endosopic Electrosurgical Suction-Irrigation Instrument), now U.S. Pat. No. 5,314,406, and Ser. No. 08/016,595 (Endoscopic Biopsy Forceps Devices With Selective Bipolar Cautery) now abandoned.

BACKGROUND OF THE INVENTION

1. Field of the Invention

This invention relates to endoscopic surgical devices. More particularly, this invention relates to an endoscopic surgical instrument having bipolar electrocautery grasping end effectors. The surgical instrument of the invention has particular application as a probe which extends through a suction-irrigation cautery instrument as set forth in Ser. No. 07/959,280.

2. State of the Art

Endoscopic surgery is widely practiced throughout the world today and its acceptance is growing rapidly. In general, endoscopic surgery involves one or more incisions made by trocars where trocar tubes are left in place-so that endoscopic surgical instruments may be inserted through the tubes. A camera or other optical instrument is often inserted through one trocar tube, while a cutter, dissector, or other surgical instrument is inserted through another trocar tube for purposes of manipulating and/or cutting the internal organ. Sometimes it is desirable to have several trocar tubes in place at once in order to receive several surgical instruments. In this manner, organ or tissue may be grasped with one surgical instrument, and simultaneously may be cut with another surgical instrument; all under view of the surgeon.

Various types of endoscopic surgical instruments are known in the art. These instruments generally comprise a slender tube containing a push rod which is axially movable within the tube by means of a handle or trigger-like actuating means. An end effector is provided at the distal end of the tube and is coupled to the push rod by means of a clevis so that axial movement of the push rod is translated to rotational or pivotal movement of the end effector. End effectors may take the form of scissors, grippers, cutting jaws, forceps, and the like.

Modern endoscopic procedures often involve the use of electrocautery. Indeed, several types of electrocautery devices for use in endoscopic surgery are described in the prior art. U.S. Pat. No. 4,418,692 to Guay, for example, discloses a device for use in laparoscopic tubal cauterization for blocking the fallopian tubes of a patient. The device comprises a substantially tubular body member having a spring-biased piston slidably mounted therein. A pair of electrodes (either monopolar or bipolar) are disposed to grasp living tissue when the piston is in a first position biased by the spring and to release the tissue when a button is pressed which moves the piston into a second position. The device includes a circuit breaker which interrupts current flowing to the electrodes when the piston is in the second position. When the electrodes grasp the tissue, current is supplied to the surface of the electrode. Guay teaches two types of grasping electrodes: a springy tweezer-like electrode pair; and a sliding J-hook type electrode.

Another electrosurgical instrument for use in combination with an endoscope is disclosed in U.S. Pat. No. 5,007,908 to Rydell for "Electrosurgical Instrument Having Needle Cutting Electrode and Spot-Coag Electrode". Rydell's device includes an elongated flexible tubular member with a plurality of lumens. The distal end of the tubular member is provided with a bullet shaped ceramic tip covered with a conductive layer and having an opening coupled to a first one of the lumens. The conductive layer is coupled to a conductor which extends through a second one of the lumens to an electrical source. A second conductor, also coupled to the electrical source is slidable through the first lumen by a plunger. The two electrodes form a bipolar pair. In a second embodiment, the conductive layer on the ceramic tip is split by an insulating gap and both halves of the tip form a bipolar pair of electrodes. Rydell's device does not provide any grasping capability.

Other electrocautery probes for use with an endoscope are disclosed in U.S. Pat. No. 3,920,021 to Hiltebrandt. Hiltebrandt discloses several types of probes similar to Rydell's in that they have a substantially bullet shaped tip with hemispheric or annular conductors forming electrode pairs. Hilterbrandt also shows electrodes similar to Guay's, a pair of springy arms slidable through a tube member to grasp and release tissue. Of course, the gripping force obtainable by either Guay's or Hiltebrandt's probes is severely limited because the electrodes must be "springy".

A bipolar electrocautery endoscopic scissors sold by Everest Medical is also known in the art and generally comprises a first fixed scissor element which is coupled to an outer tube, and a second rotating scissor element which is coupled to a push rod. The scissor elements are insulated from each other by use of ceramic layers glued to the faces of the scissors, and by an insulated pin around which the scissor element extend. Likewise, the outer tube which is connected to a first electrode wire, and the push rod which is coupled to a second electrode wire are insulated from each other, and the outer tube and push rod are coupled to a handle and actuator which effect movement of the push rod relative to the outer tube. While the Everest Medical bipolar electrocautery scissors provides the basics of a bipolar electrocautery endoscopic instrument, it has several drawbacks. In particular, the connection between the electrodes and the outer tube and push rod are by wires which are forced distally in between a ferrule and the push rod, and between an insulator on the push rod and the outer tube. This electrical connection is undesirable, however, as when the push rod and outer tube are rotated relative to the handle, electrical connection may not be properly maintained, and/or the wire contacting an uninsulated work its way proximally and end up contacting an uninsulated portion of the push rod, thereby establishing a short circuit. Moreover, because of the location of the outer tube electrode wire between the push rod and the outer tube, electrical arching is possible which could result in a short circuit between the electrodes.

SUMMARY OF THE INVENTION

It is therefore and object of the invention to provide a bipolar endoscopic electrocautery instrument having a tube and push rod having secure bipolar electrical connections to the tube and push rod.

It is also an object of the invention to provide an endoscopic electrocautery instrument having a tube and push rod coupling a proximal actuator to a pair of distal grippers where one gripper is supplied with one pole of a bipolar cautery current through the tube and the other end gripper is supplied with the other pole of a bipolar cautery current through the push rod.

It is another object of the invention to provide a handle for an endoscopic instrument having a proximal bipolar electrocautery connection to a tube and push rod of the endoscopic instrument, where the tube and push rod may be rotated relative to the handle of the instrument without disturbing the electrocautery connection.

It is a further object of the invention to provide an endoscopic instrument with a distally extending actuator which is operable by the index finger of a practitioner.

Another object of the invention is to provide an endoscopic bipolar electrocautery instrument with a proximal actuator having a force amplifying design so that the force applied at the end effectors is greater than the force applied at the actuator.

It is also an object of the invention to provide an endoscopic bipolar electrocautery instrument with a proximal insulating gas seal between the tube and the push rod.

It is still another object of the invention to an endoscopic bipolar electrocautery instrument having a pre-bent push rod which is directly connected to an end effector.

Yet another object of the invention is to provide an endoscopic bipolar electrocautery gripper instrument where gripping and electrocautery procedures are enhanced by providing gripping surfaces which are parallel when the grippers are in a position intermediate of open and closed.

In accord with these objects which will be discussed in detail below, the endoscopic bipolar electrocautery instrument of the present invention includes a proximal handle having bipolar electrical contacts therein which are separately coupled to a tube and push rod which are insulated from each other. The tube and push rod are in turn respectively coupled to a fixed distal jaw and a rotating distal jaw which are likewise insulated from each other. The tube is covered with an insulating shrink wrap from its flared distal end up to a proximal portion which is uncovered. The stationary jaw is provided with an integral clevis which is mounted inside the flared distal end of the tube thereby making electrical contact with the inner surface of the tube. The clevis holds a pair of ceramic insulators between which a movable jaw is rotatably mounted on an insulated bushing and an axle pin. A proximal end of the movable jaw is coupled to the push rod by a tang pin. The push rod is covered with an insulating shrink wrap from a point just proximal of its distal connection with the movable jaw to a point near its proximal end.

On the proximal end of the instrument, the uninsulated proximal end of the tube is mounted in a conductive bushing which is freely rotatable within a nonconductive handle. A nonconductive rotatable ferrule is mounted on a portion of the tube immediately distal of the handle. Rotation of the ferrule relative to the handle rotates the tube, push rod, and jaws relative to the handle. The proximal end of the push rod extends proximally beyond the conductive bushing and a nonconductive gas seal is fitted between the bushing and the push rod. A non-conductive actuating lever is hingedly attached to the handle and is coupled to the push rod by a ball and set screw arrangement which permits the ball, and hence the push rod to rotate relative to the actuating lever. Movement of the lever moves the push rod through the tube to open and close the distal jaws. A pair of Y-shaped electrical wiper contacts are preferably insert molded in the handle and respectively contact the bushing and uninsulated portion of the push rod on either sides of the gas seal. A bipolar cable is coupled to these contacts and is also preferably insert molded in the handle.

Preferred aspects of the invention include: forming opposing jaw faces with a distally receding angle so that teeth on the jaw faces grip more evenly; forming the clevis of the stationary jaw with protrusions which keep the ceramic insulators from rotating with the movable jaw; including a finger ring on a portion of the lever so that the jaws can be actuated by movement of a single finger; extending the lever a distance from its hinged connection with the handle to increase the force applied at the jaws; pre-bending the distal end of the push rod in order to reduce the friction between the push rod and the outer tube, and thereby reduce the amount of force required to actuate the movable jaw as well as the possibility of wearing through the insulation; and forming the ferrule with a distally extending notched neck so that the instrument may be lockingly inserted into the valve body of suction-irrigation instrument described in previously incorporated Ser. No. 07/959,280.

Additional objects and advantages of the invention will become apparent to those skilled in the art upon reference to the detailed description taken in conjunction with the provided figures.

BRIEF DESCRIPTION OF THE DRAWINGS

FIG. 7 is an enlarged side elevation view of the stationary jaw incorporating a clevis;

FIG. 7a is an enlarged top view of the jaw of FIG. 7;

FIG. 7b is an enlarged end view of the jaw of FIG. 7;

FIG. 8 is an enlarged side elevation view of the movable jaw;

FIG. 8a is an enlarged bottom view of the jaw of FIG. 8;

FIG. 8b is an enlarged end view of the jaw of FIG. 8 taken along line 8b–8b of FIG. 8;

FIG. 13 is an enlarged transparent view of the assembled distal end of the instrument of the invention with the jaws in the closed position;

FIG. 13a is a view similar to FIG. 13, but of the jaws in the open position;

FIG. 14b is a cross sectional view taken along line 14b–14b in FIG. 14a;

DETAILED DESCRIPTION OF THE PREFERRED EMBODIMENTS

Figure 1:
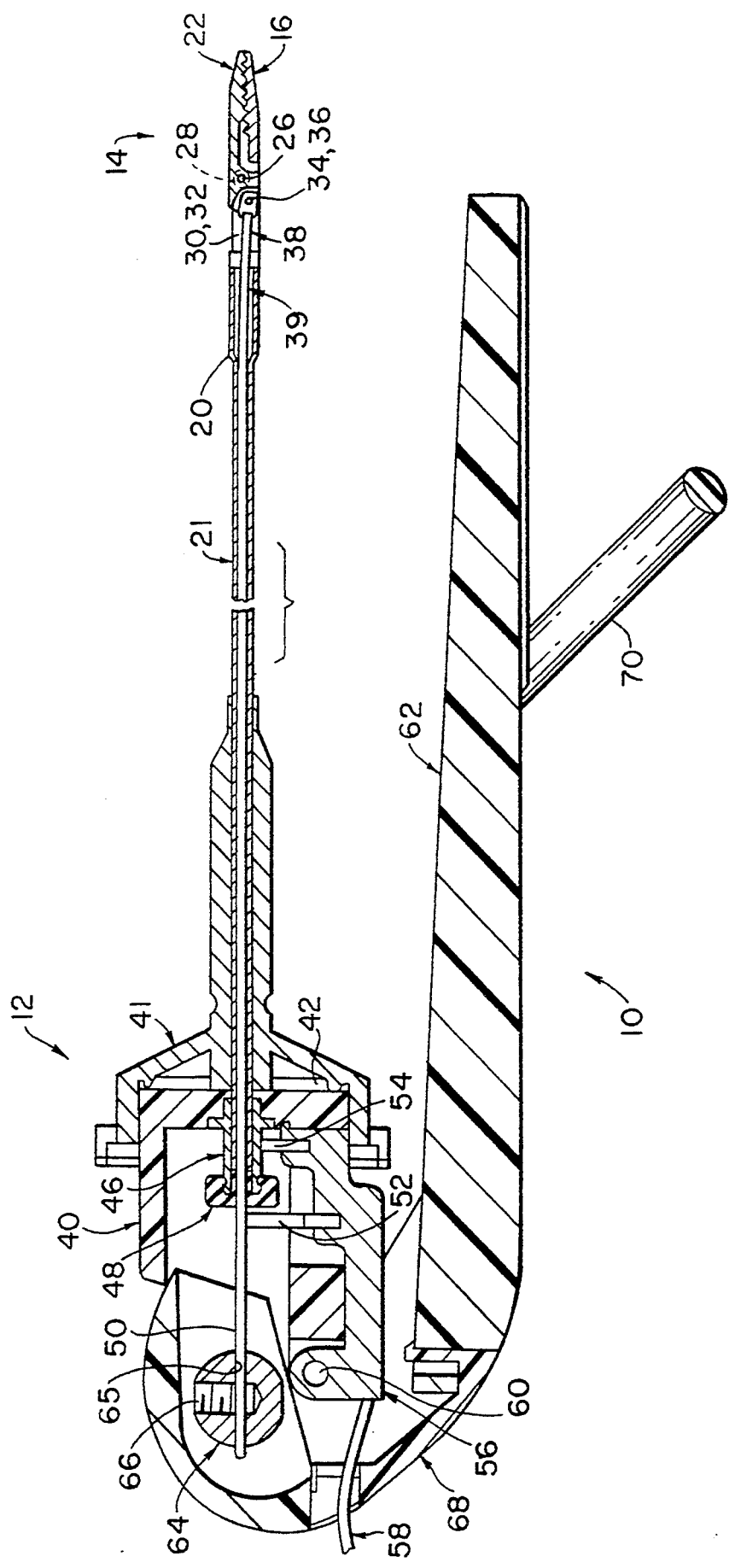
FIG. 1 is a broken longitudinal cross sectional view of the invention showing the proximal and distal ends.
Figure 2:
FIG. 2 is an enlarged side elevation view of the proximal end of the tube.
Figure 3:
FIG. 3 is an enlarged longitudinal cross sectional view of the flared distal end of the tube.
Figure 4:
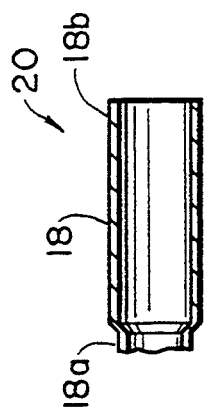
FIG. 4 is an enlarged side elevation view of the proximal end of the push rod.
Figure 6:
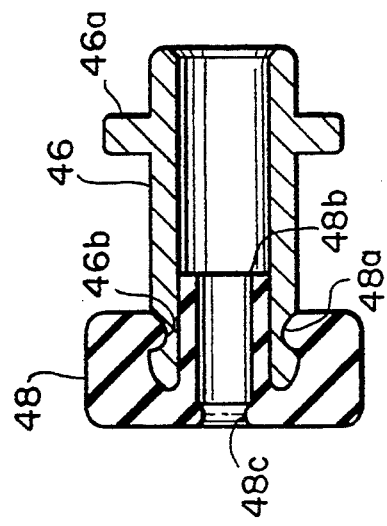
FIG. 6 is an enlarged longitudinal cross section of the handle bushing and gas seal.
Figure 5:
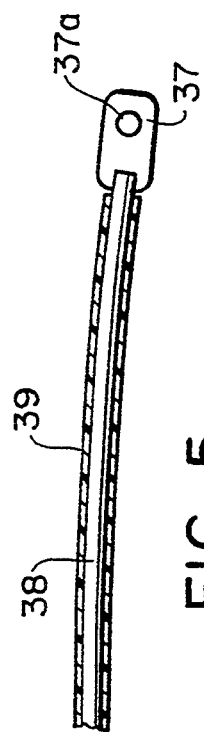
FIG. 5 is an enlarged side elevation view of the distal end of the push rod.

Turning now to FIGS. 1–6, the endoscopic bipolar electrocautery instrument 10 of the invention is shown in longitudinal cross section with a break between the proximal end 12 and the distal end 14. Starting with the distal end 14, a stationary electrically conductive jaw 16 is mounted inside the flared end 18 (FIG. 3) of an electrically conductive tube 20. A movable electrically conductive jaw 22 is rotatably mounted in a clevis portion 24 of the stationary jaw 16 by an axle pin 26 having a nonconductive bushing 28. A pair of ceramic insulators 30, 32 are placed on either side of the jaw 22 in the clevis portion 24 of stationary jaw 16 in order to electrically insulate jaw 22 from jaw 16. The movable jaw 22 is further provided with a tang 34 which is mechanically and electrically coupled by a conductive tang pin 36 to a conductive push rod 38. Push rod 38 extends axially within tube 20 to the proximal end 12 of the instrument 10. Both the push rod 38 and the tube 20 are covered with shrink-wrap insulation 39, 21 respectively along all but a portion of their length. In particular, the push rod 38 is covered with insulation except for a flattened distal end 37 which couples to the tang 34 of the movable jaw 22, and except for the proximal end 50 (FIG. 4) which makes electrical contact with a wiper described below. As seen best in FIG. 5, the distal end of the slightly flexible push rod 38 is pre-bent slightly off-axis to better couple the push rod 38 to the tang 34 of movable jaw 22 without undue rubbing against the inside of tube 20. In this manner, not only is wearing of the insulation 39 on the push rod reduced, but the force necessary to actuate the movable jaw 22 is likewise reduced.

The proximal end 12 of the instrument 10 includes an insulated handle 40 having a circular cross section and central distal opening 42 into which the tube 20 and push rod 38 extend. A ferrule 41 is attached to the tube 20 and partially covers the handle 40. The proximal end 44 of the tube 20 (FIG. 2) is not covered with shrink-wrap insulation and is mechanically and electrically coupled to a brass bushing 46 (FIG. 6) which is rotatably mounted in the central opening 42 of handle 40. Bushing 46 is provided with a flange 46a which holds the bushing inside the central opening 42 of the handle 40, and an annular groove 46b for receiving and holding a rubber seal 48. Rubber seal 48 is provided with an inner extending lip 48a which engages the annular groove 46b of the bushing. A tubular portion 48b of the seal 48 extends into the proximal end of the bushing 46, and a sealing lip 48c engages the push rod 38. Rubber seal 48 provides a gas-tight seal between the push rod 38 and the tube 20 and also provides additional electrical insulation between the push rod and the conductive bushing 46.

According to the preferred embodiment of the invention, a pair of Y-shaped electrical wiper contacts 52, 54 are insert molded in a cable assembly 56 and mounted inside the handle 40 as will be described in more detail below. Contacts 52, 54 are coupled to a bipolar cable 58 which in turn is coupled to a source of cautery current (not shown). The handle 40 is further provided with a rivet or axle 60 which is laterally offset from and perpendicular to the longitudinal axes of tube 20 and push rod 38, and which couples the handle to a substantially J-shaped lever 62 which is mounted for rotation on the axle 60. The proximal end of lever 62 is provided with a ball coupling 64 having a diametrical bore 65 and a set screw 66 which intersects the bore 65. The proximal end of push rod 38 is inserted into the bore 65 and fastened to the ball coupling 64 by the set screw 66. Lever 62 is also provided with a cable cover 68 through which bipolar cable 58 passes. The J-shaped lever 62 extends distally from the handle, and a finger ring 70 is provided near the distal end of the lever 62.

Those skilled in the art will appreciate that rotation of lever 62 moves the pushrod 38 relative to the tube 20 and rotates the movable jaw 22 about the axle 26. The length of lever 62 magnifies the force applied to it so that a relatively small force applied by the finger of a practitioner inserted in the finger ring 70 results in a much stronger gripping force between jaws 16, 22. It will also be appreciated that rotation of ferrule 41 rotates both the tube 20 and the jaws 16, 22 about the longitudinal axis of the instrument 10. The ball coupling 64 in the handle 62 allows the push rod 38 (and the ball 64) to rotate relative to the handle. However, the Y-shaped wiper contacts 52, 54 maintain a good electrical contact with the tube and the push rod regardless of the angular position of the tube and push rod, as the wiper contacts are in the handle and do not move.

Turning now to FIGS. 7 through 12a, components of the distal end of the instrument are shown in greater detail. The stationary jaw 16 is shown in detail in FIGS. 7–7b. There it can be seen that the jaw has a generally cylindrical stepped diameter proximal portion including cylindrical steps 76, 78, and 80. Extending therefrom is the distal end effector 71 having a centrally located integral clevis portion 24 and a gripping surface 72. Comparing the proximal portion of the jaw 16 with the flared distal end of the tube 20 in FIG. 3, and as shown in the enlarged assembled view of FIG. 13, it will be appreciated that the smallest diameter proximal end 80 of jaw 16 is dimensioned to fit inside the smaller diameter portion 18a of the distal end 18 of tube 20. The next larger diameter portion 78 of jaw 16 is dimensioned to fit inside the larger diameter portion 18b of the flared distal end 18 of tube 20. The largest diameter portion 76 of the proximal end of the jaw 16 has an outer diameter substantially equal to the outer diameter of the larger diameter portion 18b of the flared distal end of tube 20. The centrally located clevis portion 24 of jaw 16 is a substantially rectangular opening which extends from the top of the jaw through the bottom of the jaw. The clevis portion 24 communicates with the interior of tube 20 by a longitudinal bore 75 which extends from the proximal end of the clevis portion 24 through the stepped diameter portions 76, 78, 80. As seen best in FIG. 7b, bore 75 extends through the bottom 74 of the proximal portion of the jaw, thus leaving an opening in the bottom of the jaw from the proximal end through to the distal end of the clevis opening 24. Those skilled in the art will appreciate that this bottom opening 74 accommodates the pre-bent distal end of push rod 38 as shown in FIGS. 1, 5, 13, and 13a. The clevis portion 24 of jaw 16 is also provided with axle holes 86, 87 for mounting movable jaw 22 as described in detail below. Hole 86 has a relatively larger diameter than hole 87 and hole 87 has an outward flare 87a. The proximal end of clevis portion 24 is provided with two steps or protrusions 82, 84 and the distal end of the clevis portion is provided with ramped edges 90, 91. A proximal floor portion 73 of the end effector 71 extends proximally below the ramped edges 90, 91. The protrusions 82 84 and floor portion 73 hold ceramic insulators 30, 32 mentioned above and described in detail below.

FIGS. 8, 8a, and 8b show details of the movable jaw 22. The movable jaw 22 has a distal semi-cylindrical portion 108 with a lower gripping surface 110, and an intermediate portion 112, and a proximal tang 34. Intermediate portion 112 is provided with an axle hole 114 for receiving ceramic bushing 28 and axle pin 26 as described in detail below. The tang 34 is split into parallel arms 118, 119 between which the distal end 37 of push rod 38 fits as described below. The parallel arms 118, 119 are provided with coupling holes 116, 117 for receiving the tang pin 36 as described below.

Figure 9:
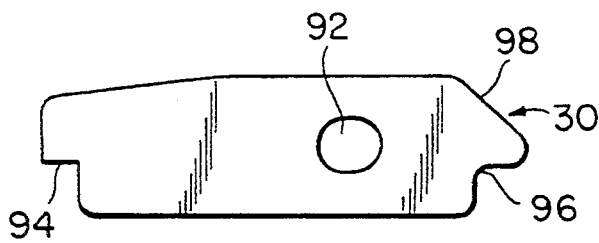
FIG. 9 is an enlarged side elevation view of one of the two ceramic insulators used to insulate the movable jaw from the clevis of the stationary jaw.
Figure 9A:
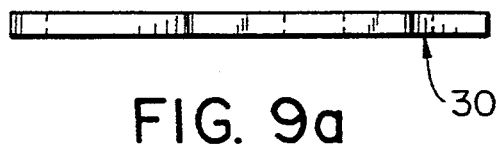
FIG. 9a is an enlarged top view of the insulator of FIG. 9.

FIGS. 9 and 9a show details of the ceramic insulator 30 which take the form of elongated, shaped washers. Comparing FIGS. 7, 8, and 9, it will be appreciated that the insulator 30 has a profile substantially matching the profile of the clevis portion 24 of jaw 16 and corresponding in part to the profile of the intermediate portion 112 of jaw 22. Insulator 30 has a central hole 92, a lower proximal notch 94, a lower distal notch 96 and an upper distal ramp 98. Insulator 30 is placed inside the clevis portion 24 of jaw 16 so that its lower proximal notch 94 rests on top of protrusion 82; its lower distal notch 96 rests on floor portion 73; its ramp 98 aligns with ramp 90; and its central hole aligns with hole 87. An identical ceramic insulator 32 (FIGS. 1, 13, and 13a) is placed inside clevis portion 24 aligning with step 84, hole 86, ramp 91 and floor 73. The two insulators 30, 32 thereby line the inner walls of clevis 24 and prevent contact between the movable jaw 22 and clevis 24. As an alternate to the elongated, shaped ceramic insulating washers, two medical grade, high Durometer silicone washers may be used. The silicone washers may be round or otherwise shaped as desired and provide a good degree of insulation. In addition, the silicone washers effectively seal against the movable jaw 22, thereby ensuring that the ceramic bushing 28 around which the movable jaw 22 rotates is kept entirely within the jaw 22 and the silicone washers.

Figure 10:
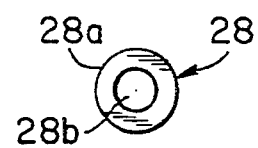
FIG. 10 is an enlarged side elevation view of the insulating bushing used to mount the movable jaw in the clevis of the stationary jaw.
Figure 10A:
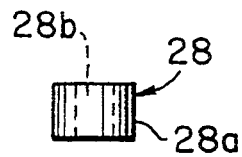
FIG. 10a is an enlarged top view of the bushing of FIG. 10.
Figure 11:
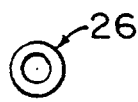
FIG. 11 is an enlarged side elevation view of the axle pin which fits inside the insulated bushing.
Figure 11A:
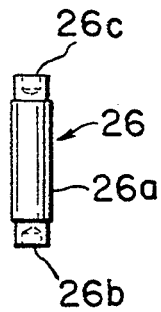
FIG. 11a is an enlarged top view of the axle pin of FIG. 11.

FIGS. 10 and 10a show the ceramic bushing 28 around which the movable jaw 22 rotates, and FIGS. 11 and 11a show the axle pin 26 which extends through the ceramic bushing. The ceramic bushing 28 has an outer diameter 28a dimensioned to fit comfortably within the hole 114 in movable jaw 22 and in the holes 92 of the ceramic (or silicone) insulators 30, 32, and an inner diameter 28b dimensioned to accept axle pin 26. The ceramic bushing extends across the longitudinal axis of the surgical instrument from insulator 30 to insulator 32. The axle pin 26 has a relatively wide body 26a which extends through the insulator 32 and provides strength to the bushing, and slightly narrower tips 26b, 26c. At least one of the tips preferably has a small counterbore therein so that the tip may be spread in the flared hole 87a of the clevis of jaw 16 by a riveting instrument during assembly.

Figure 12:
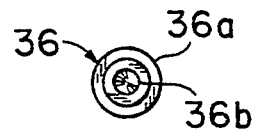
FIG. 12 is an enlarged side elevation view of the tang pin used to couple the movable jaw and the push rod.
Figure 12A:
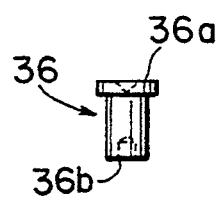
FIG. 12a is an enlarged top view of the tang pin of FIG. 12.

FIGS. 12 and 12a show the tang pin 36. Tang pin 36 has a flat head 36a and a distal counterbore 36b which is spread in assembly to form a rivet-like connection between the distal end 37 of the push rod 20 and the hole 116 in the tang 34 of the movable gripper jaw 22.

Turning now to FIGS. 13 and 13a and with reference to FIGS. 7–12a, when assembling the distal end 14 of the instrument 10, the two ceramic insulators 30, 32 are inserted into the clevis opening 24 in the stationary jaw 16 as described above. The ceramic bushing 28 is inserted into the hole 114 in movable jaw 22 and both are inserted into the space between the insulators 30, 32 until the opening 28b in the bushing 28 aligns with the holes 86, 87 in the jaw 16. The axle pin 26 is then inserted into hole 86 of the jaw 16 with its counterbored narrow end 26b facing narrower diameter hole 87. The counterbored narrow end 26b is then spread in tapered hole 87a by a riveting instrument. The distal end 37 of the push rod 38 is then coupled to the tang 34 by inserting the flattened distal end 37 between arms 118, 119 until the hole 37a aligns with the holes 116, 117. Tang pin 36 is then inserted and spread with a riveting instrument.

As seen in FIG. 13, when the distal end 14 of instrument 10 is assembled, the gripping surfaces 110, 72 of jaws 22, 16 are not parallel when the jaws are in the closed position. Rather, these surfaces (defined by the apex of the ribs or teeth 110a, 72a, of the jaws) mate at the distal end of the jaws, and are angled away from each other in the proximal direction as indicated by angle "A" such that the ribs or teeth 110a, 72a do not touch at their proximal end. By forming the gripping surfaces this way, when the jaws are gripping an object, a better gripping action is achieved. In particular, the angle of the gripping surfaces are chosen such that when the jaws are gripping an object that they are likely to encounter, the jaws assume a parallel position which is intermediate their open and closed positions.

Figure 14:
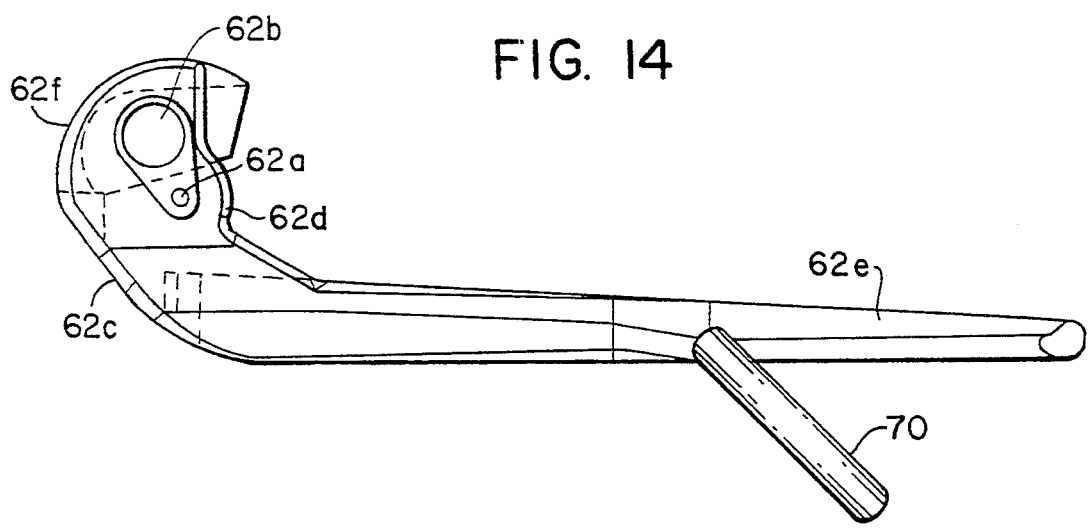
FIG. 14 is a side elevation view of the lever actuator of the instrument of the invention.
Figure 14A:
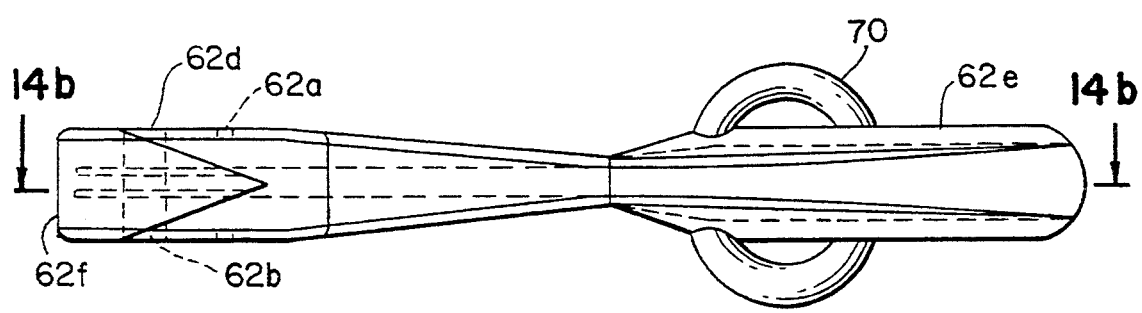
FIG. 14a is a bottom view of the lever actuator.
Figure 14B:
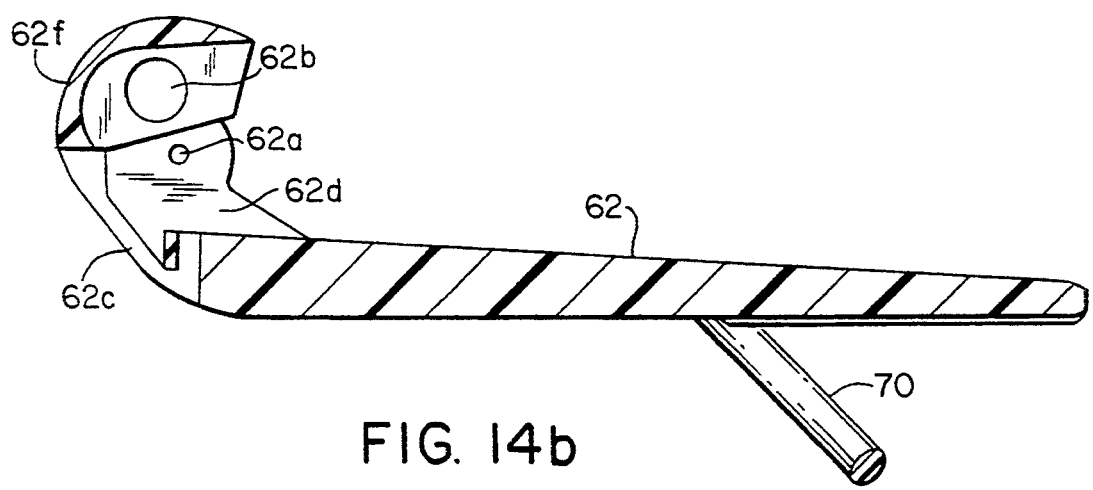

FIGS. 14 through 18a show components of the proximal end of the instrument in greater detail. As mentioned above, the actuating lever 62 (shown in detail in FIGS. 14, 14a, and 14b) is a substantially J-shaped member which extends from the proximal end 12 of the instrument 10 towards its distal end 14 (FIG. 1). At its proximal end, the actuator has a pivot bore 62a in a handle receiving space 62d which permits the actuator lever to be coupled to the insulated handle 40 as described below. The proximal end of lever 62 includes a ball receiving opening 62b which receives the rotating ball 64 (which is coupled to the push rod), and a cable receiving opening 62c through which a bipolar cable 58 extends. The distal end of the lever 62 has a broadened paddle portion 62e which extends anywhere from between two to five inches (and preferably at least four inches) distally. Extending from the distal end of the paddle portion 62e and at a preferred angle of approximately forty-five degrees is a finger ring 70. The lever is preferably a molded plastic piece which is shaped such that the proximal end 62f of the lever is rounded and narrow and fits ergonomically in the palm of the hand of the practitioner when the hand is cupped with the thumb being parallel to the middle finger (to actuate rotation of the device as discussed hereinafter), while the paddle portion 62e substantially parallels the longitudinal axis of the instrument such that the pointer digit of the practitioner can slip into the finger ring 70. Because force to the actuator is applied at the finger ring location, and that location is removed from the pivot bore 62a rotation location, the forces applied to the push rod are amplified accordingly.

Figure 15:
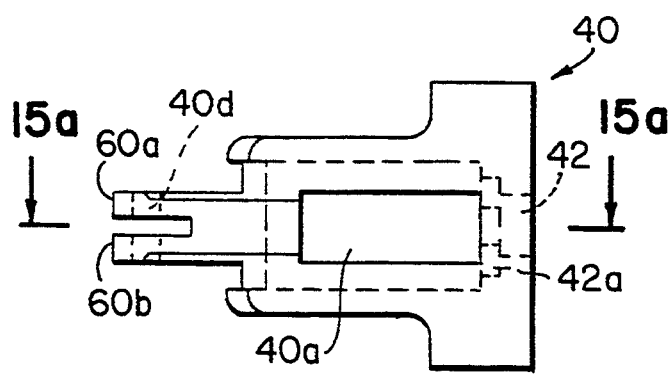
FIG. 15 is bottom view of the insulated handle of the instrument of the invention.
Figure 15A:
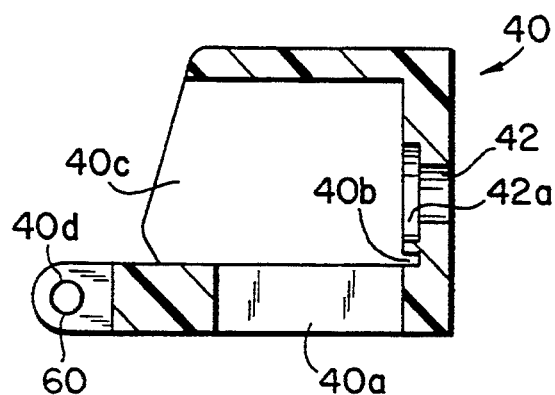
FIG. 15a is a cross sectional view taken along line 15a–15a of FIG. 15.
Figure 16:
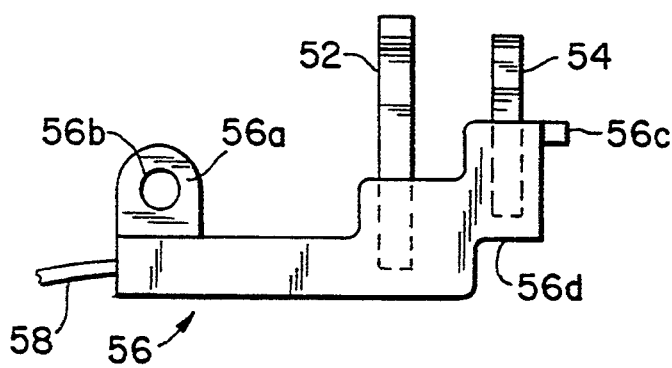
FIG. 16 is a side elevation view of the cable assembly.

Turning to FIGS. 15 and 15a, the insulated handle 40 is seen. The handle 40 is a substantially cylindrical member provided with a substantially rectangular lower opening 40a for receiving a cable assembly 56 (FIG. 16). The handle also has a pair of arms 60a, 60b which define a slot for a tab 56a of the cable assembly. The arms include holes 40d for receiving an actuator axle 60. The handle 40 also includes a distal opening 42 which is provided with a seat or recess 42a for receiving the flange 46a of bushing 46. A horizontal key slot 40b is located between the opening 40a and seat 42a for receiving a key 56c of the cable assembly. A substantially rectangular proximal opening 40c faces and receives a portion of the proximal end of the lever 62.

Figure 16B:
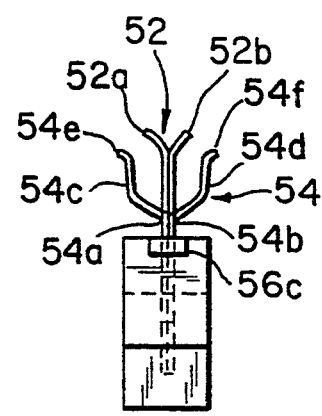
FIG. 16b is a distal end view of the cable assembly.
Figure 16A:
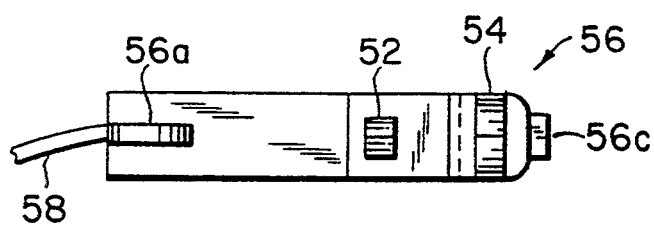
FIG. 16a is a top-view of the cable assembly.

The cable assembly 56 of the invention is seen in FIGS. 16 and 16a and includes a proximal vertical tab 56a having a hole 56b therein, a distal horizontal key 56c, and a distal notch 56d. Two Y-shaped wipers 52 and 54 which are coupled to separate wires of bipolar cable 58 which is preferably insert molded in the cable assembly are themselves preferably insert molded in the cable assembly 56. The Y-shaped wipers 52, 54 are spaced apart, with wiper 52 being proximal of wiper 54. It will be appreciated that wiper 54 provides electrical contact to the tube 20 (FIG. 1) and is wider and shorter then wiper 52 which provides electrical contact to the push rod 38 (FIG. 1). According to a presently preferred embodiment, the wipers are constructed of a pair of resilient conductive strips which are pre-bent as seen best in FIG. 16b. In particular, wiper 54, which provides contact to the tube 20 is provided with first lower bends 54a, 54b having angles of approximately 42 degrees from vertical. Second intermediate bends 54c, 54d bring the wiper blades into a substantially vertical spaced apart position and upper outward bends 54e, 54f provide a smooth entry for the tube 20. It will be appreciated that the distance between the blades of wiper 54 is smaller than the outer diameter of the tube 20 and that the blades are resilient enough to grip against the tube 20. Wiper 54, which provides contact to the push rod 37 are provided only with upper bends 52a, 52b which provide a smooth entry for the push rod between the blades of the wiper 52. The cable assembly 56 is inserted into the handle 40 in a manner discussed below.

Figure 17:
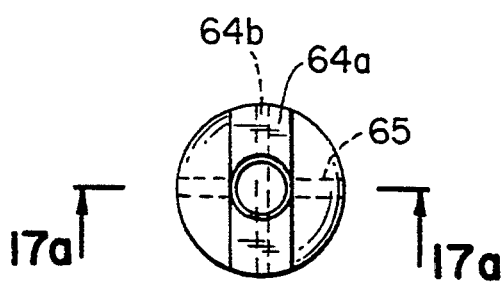
FIG. 17 is a top view of the ball coupling for use in the lever.
Figure 17A:
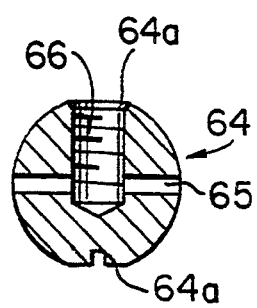
FIG. 17a is a cross sectional view taken along line 17a–17a in FIG. 17.

The coupling ball 64 which couples to the push rod and permits rotation of the push rod relative to the handle 40 and actuating lever 62 is shown in more detail in FIGS. 17 and 17a. The ball 64 has flattened surface portions 64a which permit insertion of the ball 64 into the opening 62b of the lever 62, a first bore 65 for receiving the push rod 38, and a second bore 66 for receiving a set screw (not shown) which fixes the push rod in the ball 64. A circumferential groove 64b which runs diametrically relative to bore 65 is provided for permitting a thin screwdriver or the like to engage the ball while the set screw is being inserted during assembly so that the push rod will not be bent due to the force exerted on the set screw.

Figure 18:
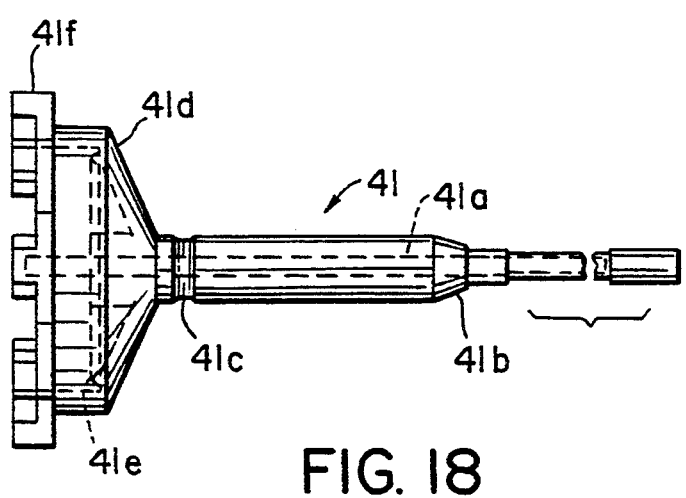
FIG. 18 is a side elevation view of the ferrule.
Figure 18A:
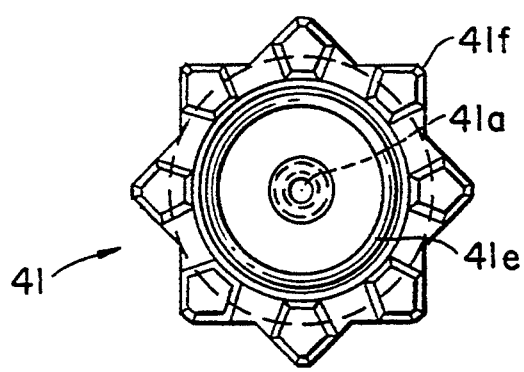
FIG. 18a is a proximal end view of the ferrule.

A final component of the preferred instrument of the invention is a ferrule 41 which is shown in detail in FIGS. 18 and 18a. The ferrule 41 extends around and is used for rotation the outer tube 20. The ferrule 41 has a central bore 41a through which the tube 20 extends, a tapered distal end 41b, an intermediate groove 41c, a flared proximal portion 41d with an inner circular flange 41e, and outer finger gripping protrusions 41f. Those skilled in the art will appreciate that the circular flange 41e provides a friction reducing interface between the ferrule and the handle so that rotation of the ferrule is not impeded, while the finger gripping protrusions 41f are provided to permit the practitioner to cause a rotation of the ferrule 41, and hence the outer tube 20, grippers 16, 22, etc.

Comparing FIGS. 15–18a and FIG. 1, those skilled in the art will appreciate that after the distal end 14 of the instrument 10 is assembled as described above, the ferrule 41 is mounted on the tube 20 by press fitting. The proximal ends of tube 20 and push rod 38 are then inserted into the distal opening 42 of the handle 40. Bushing 46 is press fit to tube 20 so that flange 46a rests inside the recessed seat 42a of opening 42 and the seal 48 is attached to the proximal end of the bushing as described above. The cable assembly 56 is inserted into the bottom opening 40a of the handle 40 so that its horizontal key enters slot 40b and its lower distal notch 56d enters the flared proximal portion of the ferrule 41. The vertical tab 56a of the cable assembly is then inserted between arms 60a and 60b until the hole 56b aligns with the holes in the arms 60a, 60b. As the cable assembly is inserted into the handle, the widened ends 52a, 52b of wiper 52 spread the wiper 52 around the push rod to embrace it and the widened ends 54e, 54f of the wiper 54 spread the wiper 54 around the tube to embrace it. The ball coupling 64 is inserted into the ball receiving opening 62b in lever 62 and rotated so that it can receive the proximal end of the push rod 38. Wires 58 from cable assembly 56 are threaded through the opening 62c in the lever 62 and the lever is aligned with the handle so that arms 60a, 60b holding vertical tab 56a enter the space 62d in the lever 62. The proximal end of the push rod 38 is directed through bore 65 of ball 64. An axle pin 60 is then inserted through holes 62a, 56b in the lever 62 and the handle 56. Cable cover 68 is then snapped over the opening 62c. Upon setting of the end effectors in their closed position, the set screw (not shown) screwed into the set screw bore 66 in the ball 64, and a cover (not shown) is snapped over the opening 62b.

The operation of the endoscopic bipolar electrocautery instrument with grasping end effectors is as follows. The distal end 14 of the instrument 10 is inserted into a trocar tube in a conventional manner. The practitioner grasps the proximal end 12 of the instrument 10 by inserting an index finger through finger ring 70 and, if desired, by gripping ferrule 41 with a thumb and a middle finger. Cautery current may be controlled through a conventional foot switch (not shown). Movement of the index finger of the practitioner opens and closes the jaws as described above. In addition, rotation of the ferrule rotates the jaws about the longitudinal axis of the instrument. As mentioned above, the instrument of the invention is designed so that it can be used advantageously with an endoscopic suction-irrigation instrument described in Ser. No. 07/959,280. Thus, the instrument 10 of the invention may be inserted into the fluid chamber of the suction-irrigation instrument until the instrument 10 is locked in place by the locking pin engaging the groove 41c in ferrule 41. The instrument 10 conveniently fits with the lever 62 alongside the pistol shaped handle of the suction-irrigation instrument so that the lever can be operated by the index finger of the practitioner while the practitioner holds the pistol-grip handle of the suction-irrigation instrument.

There have been described and illustrated herein the preferred embodiment of an endoscopic bipolar electrocautery instrument with grasping end effectors. While particular embodiments of the invention have been described, it is not intended that the invention be limited thereto, as it is intended that the invention be as broad in scope as the art will allow and that the specification be read likewise. Thus, while particular end effectors have been disclosed, it will be appreciated that other types of end effectors could be utilized with the instrument. Also, while particular devices have been shown to insulate one jaw from the other, it will be recognized that other types of insulating devices could be used with similar results obtained. Moreover, while particular configurations have been disclosed in reference to the bushing, seal, and wiper contacts, it will be appreciated that other configurations could be used as well. Furthermore, while a J-shaped actuator having a finger ring has been described as being advantageous, it will be understood that different types of actuators can achieve a similar function. It will therefore be appreciated by those skilled in the art that yet other modifications could be made to the provided invention without deviating from its spirit and scope as so claimed.

We claim:

1. An endoscopic bipolar electrocautery instrument comprising:
    a) a hollow electrically conductive tube having a proximal end and a distal end, said tube being covered with an outer first electrically insulating wrap except for a non-insulated outer proximal portion of said tube;
    b) an electrically conductive rod having a proximal end and a distal end, said rod being covered with a second electrically insulating wrap except for proximal and distal non-insulated portions of said rod, said rod extending through said tube;
    c) an electrically nonconductive handle coupled to said proximal end of said tube;
    d) a first electrically conductive end effector mechanically and electrically coupled to said tube;
    e) a second electrically conductive end effector electrically and mechanically coupled to said non-insulated distal end portion of said rod and pivoting relative to said tube;
    f) insulating means for electrically insulating said second electrically conductive end effector from said first electrically conductive end effector;
    g) actuating means mechanically coupled to said handle means and to said proximal end of said rod for imparting reciprocal motion to said rod relative to said tube which is translated to pivotal motion of said second end effector;
    h) first electrical contact means mounted in said handle means for electrically coupling with said non-insulated outer proximal portion of said tube; and
    i) second electrical contract means mounted in said handle means for electrically coupling with said non-insulated proximal portion of said rod, wherein said proximal end of said tube is rotatable relative to said handle, and said first and second electrical contact means respectively include first and second wiper contacts which are stationary relative to said handle, said first wiper contact maintaining a wiping electrical coupling with said tube and said second wiper contact maintaining a wiping electrical coupling with said rod as said tube and rod are rotated relative to said handle and said first and second wiper contacts.

2. An endoscopic instrument according to claim 1, further comprising:
    j) a bushing mechanically and electrically coupled to said proximal end of said tube, said bushing rotatingly engaging said handle means,
    wherein said mechanical coupling of said actuating means to said rod includes rotational means, and said bushing and said rotational means allow rotation of said tube and rod relative to said handle means and said actuation means.

3. An endoscopic instrument according to claim 2, further comprising:
    k) a ferrule means coupled to said tube at a point distal of said handle for gripping said tube and rotating said tube relative to said handle.

4. An endoscopic instrument according to claim 3, wherein:
    said ferrule includes a tapered distal tip, a flared proximal turning ring and an annular notch between said ring and said tip.

5. An endoscopic instrument according to claim 2, wherein:
    said rotational means comprises a ball having a first passage into which said rod extends.

6. An endoscopic instrument according to claim 2, wherein:
    a proximal end of said bushing is covered with an electrically insulating material.

7. An endoscopic instrument according to claim 6, wherein:
    said electrically insulating material comprises a rubber plug having an inner extending cylindrical portion and an outer extending cylindrical portion with an annular space therebetween, said inner extending cylindrical portion lining an inner surface of said bushing and said outer extending cylindrical portion covering an outer surface of said bushing, said proximal end of said bushing residing in said annular space.

8. An endoscopic instrument according to claim 7, wherein:
    said bushing has an annular groove and said outer extending cylindrical portion of said rubber plug has an inner extending lip, said lip engaging said groove.

9. An endoscopic instrument according to claim 2, wherein:
    said bushing has a flange and said handle means has a flange receiving recess, said bushing engaging said handle by said flange residing in said flange receiving recess.

10. An endoscopic instrument according to claim 1, wherein:
at least one said first and second wiper contacts is substantially Y-shaped.

11. An endoscopic instrument according to claim 10, wherein:
said first and second wiper contacts are insert molded in a nonconductive member attached to said handle means.

12. An endoscopic instrument according to claim 1, further comprising:
j) an electrically conductive clevis mechanically and electrically coupled between said distal end of said tube and said first electrically conductive end effector, wherein
said first electrically conductive end effector and said clevis are an integral piece, and
said insulating means comprises a pair of insulating washers and a ceramic bushing, with said ceramic bushing extending through a hole in said second end effector.

13. An endoscopic instrument according to claim 1, wherein:
said first and second electrical contact means are coupled to bipolar cable means and said actuating means is provided with a passage through which said bipolar cable means exits said handle means.

14. An endoscopic instrument according to claim 1, wherein:
said distal end of said rod is pre-bent away from its longitudinal axis.

15. An endoscopic instrument according to claim 14, wherein:
said distal end of said rod is bent to a distance of approximately one half of its diameter from its longitudinal axis and is provided with enough flexibility to flex the same distance.

16. An endoscopic instrument according to claim 1, wherein: said handle means comprises,
i) a distal opening for receiving said proximal end of said tube,
ii) a proximal opening for receiving a portion of said actuating means, and
iii) a lateral opening for receiving said first and second electrical contact means.

17. An endoscopic instrument according to claim 16, wherein:
said handle means further comprises,
iv) a pivot hole in a portion of said handle means between said proximal opening and said lateral opening, said pivot hole receiving a pivot means for pivotally mounting said actuating means.

18. An endoscopic instrument according to claim 17, wherein:
said pivot hole has an axis and said portion of said handle means containing said pivot hole is provided with a first slot transecting said axis.

19. An endoscopic instrument according to claim 18, wherein:
said first and second electrical contact means are carried on a nonconductive member having an extending first tab with a hole in said first tab, and
said nonconductive member being coupled to said handle means by inserting said first tab into said first slot so that said hole in said first tab substantially aligns with said pivot hole.

20. An endoscopic instrument according to claim 19, wherein:
said handle means is further provided with first engaging means located between said lateral opening and said distal opening, and
said nonconductive member is provided with second engaging means so that said nonconductive member is additionally coupled to said handle means by a coupling of said first and second engaging means.

21. An endoscopic instrument according to claim 20, wherein:
said first engaging means is a second slot and said second engaging means is a second tab.

22. An endoscopic instrument according to claim 21, wherein:
said first slot is substantially perpendicular to said second slot.

23. A bipolar endoscopic surgical instrument comprising:
a) a hollow electrically conductive tube having a proximal end and a distal end, said tube being covered with an outer first electrically insulating wrap except for an electrical contact receiving non-insulated outer proximal portion of said tube;
b) an electrically conductive rod having a proximal end and a distal end, said rod being covered with a second electrically insulating wrap except for an electrical contact receiving non-insulated outer proximal portion of said rod and an outer distal portion of said rod, said rod extending through said tube;
c) an electrically non-conductive handle coupled to said proximal end of said tube;
d) a first electrically conductive end effector mechanically and electrically coupled to said tube;
e) a second electrically conductive end effector electrically and mechanically coupled to said distal end of said rod and pivoting relative to said tube;
f) first insulating means for electrically insulating said second electrically conductive end effector from said first electrically conductive end effector;
g) actuating means mechanically coupled to said handle means and said proximal end of said rod for imparting reciprocal motion to said rod relative to said tube which is translated to pivoting motion of said second end effector;
h) second insulating means for electrically insulating said electrical contact receiving non-insulated outer proximal portion of said rod from said tube during said reciprocal motion; and
i) a bushing coupled to said proximal end of said tube, wherein said second insulating means comprises a rubber plug having an inner extending cylindrical portion and an outer extending cylindrical portion with an annular space therebetween, said inner extending cylindrical portion lining an inner surface of said bushing and said outer extending cylindrical portion covering an outer surface of said bushing, a proximal end of said bushing residing in said annular space.

24. An bipolar endoscopic instrument according to claim 23, wherein:
said second insulating means is a rubber sealing gasket.

25. An bipolar endoscopic instrument according to claim 23, wherein:
said bushing has an annular groove and said outer extending cylindrical portion of said rubber plug has an inner extending lip, said lip engaging said groove.

26. An bipolar endoscopic instrument according to claim 23, further comprising:
  i) an electrically conductive clevis mechanically and electrically coupled between said distal end of said tube and said first electrically conductive end effector, wherein,
  said first insulating means electrically insulates said second electrically conductive end effector from said clevis.

* * * * *